(12) United States Patent
O'Brien et al.

(10) Patent No.: US 11,844,877 B2
(45) Date of Patent: Dec. 19, 2023

(54) DEVICES AND METHODS FOR NERVE REGENERATION

(71) Applicant: Integra LifeSciences Corporation, Princeton, NJ (US)

(72) Inventors: Fergal O'Brien, Dublin (IE); Alan Hibbitts, Kildare (IE); Simon James Archibald, Pennington, NJ (US)

(73) Assignee: Integra LifeSciences Corporation, Princeton, NJ (US)

( * ) Notice: Subject to any disclaimer, the term of this patent is extended or adjusted under 35 U.S.C. 154(b) by 100 days.

(21) Appl. No.: 17/222,026

(22) Filed: Apr. 5, 2021

(65) Prior Publication Data

US 2021/0308330 A1    Oct. 7, 2021

Related U.S. Application Data

(60) Provisional application No. 63/005,585, filed on Apr. 6, 2020.

(51) Int. Cl.
| | | |
|---|---|---|
| *A61L 27/36* | (2006.01) | |
| *A61L 27/22* | (2006.01) | |
| *A61L 27/24* | (2006.01) | |

(52) U.S. Cl.
CPC ......... *A61L 27/3675* (2013.01); *A61L 27/225* (2013.01); *A61L 27/24* (2013.01); *A61L 27/3683* (2013.01); *A61L 2300/236* (2013.01); *A61L 2300/252* (2013.01); *A61L 2430/32* (2013.01)

(58) Field of Classification Search
CPC .... A61L 27/3675; A61L 27/225; A61L 27/24; A61L 27/3683
See application file for complete search history.

(56) References Cited

U.S. PATENT DOCUMENTS

| | | |
|---|---|---|
| 4,778,467 A | 10/1988 | Stensaas et al. |
| 4,877,029 A | 7/1989 | Valentini et al. |
| 4,955,893 A | 9/1990 | Yannas et al. |
| 4,963,146 A | 10/1990 | Li |
| 5,011,486 A | 4/1991 | Aebischer et al. |
| 5,019,087 A | 5/1991 | Nichols |
| 5,026,381 A | 6/1991 | Li |
| 5,092,871 A | 3/1992 | Aebischer et al. |
| 5,502,092 A | 3/1996 | Barrows et al. |
| 5,656,605 A | 8/1997 | Hansson et al. |
| 5,925,053 A | 7/1999 | Hadlock et al. |
| 5,948,654 A | 9/1999 | Tranquillo et al. |
| 5,997,895 A | 12/1999 | Natoram et al. |
| 6,057,137 A | 5/2000 | Tranquillo et al. |
| 6,214,021 B1 | 4/2001 | Hadlock et al. |
| 6,447,701 B1 | 9/2002 | Heschel et al. |
| 6,461,629 B1 | 10/2002 | Tranquillo et al. |
| 6,899,873 B2 | 5/2005 | Ma et al. |
| 6,969,523 B1 | 11/2005 | Mattern et al. |
| 7,198,799 B2 | 4/2007 | Mueller et al. |
| 10,940,235 B2 | 3/2021 | Kohn et al. |
| 2001/0031974 A1 | 10/2001 | Hadlock et al. |
| 2002/0018799 A1 | 2/2002 | Spector |
| 2002/0150753 A1 | 10/2002 | Ma et al. |
| 2003/0176876 A1 | 9/2003 | Chen et al. |
| 2005/0013844 A1 | 1/2005 | Hadlock et al. |
| 2011/0129515 A1 | 6/2011 | Archibald |
| 2015/0073564 A1 | 3/2015 | Valmikinathan et al. |
| 2019/0357910 A1 | 11/2019 | Archibald et al. |

FOREIGN PATENT DOCUMENTS

| | | | | |
|---|---|---|---|---|
| WO | WO-2011047970 A1 | * | 4/2011 | ......... A61B 17/1128 |
| WO | WO-2016077839 A1 | * | 5/2016 | ......... A61B 17/1128 |

OTHER PUBLICATIONS

Evercooren et al. Nerve growth factor, laminin, and fibronectin promote neurite growth in human fetal sensory ganglia cultures. J. Neurosci. Res., 8: 179-193, 1982 (Year: 1982).*
Plantman et al. Integrin-laminin interactions controlling neurite outgrowth from adult DRG neurons in vitro. Molecular and Cellular Neurosicence. vol. 39, Issue 1, 2008, pp. 50-62 (Year: 2008).*
Spearman et al. Tissue-Engineered Peripheral Nerve Interfaces. Advanced Functional Materials. 2017, 1701713 (Year: 2017).*
Dyck et al. Chondroitin sulfate proteoglycans: Key modulators in the developing and pathologic central nervous system. Experimental Neurology 269 (2015) 169-187 (Year: 2015).*
Chawla. Peripheral Nervous System Anatomy, Medscape, 2016 (Year: 2016).*
Haugh et al. Novel Freeze-Drying Methods to Produce a Range of Collagen-Glycosaminoglycan Scaffolds with Tailored Mean Pore Sizes. Tissue Engineering. vol. 16, No. 5, 2010 (Year: 2010).*
Damink et al. J Mater Sci Mater Med. 1995; 6: 460-472. (Year: 1995).
Paul et al. The Scientific World Journal. 2003; 3: 138-155. (Year: 2003).

(Continued)

*Primary Examiner* — Robert A Wax
*Assistant Examiner* — John Seungjai Kwon
(74) *Attorney, Agent, or Firm* — Eva Tan

(57) ABSTRACT

A nerve regeneration device comprising a bioresorbable conduit and a matrix contained therein having elongate pores aligned with the longitudinal axis of the conduit. The matrix comprises collagen, fibronectin, laminin-1, and laminin-2, wherein the amount, by weight, of laminin-1 or laminin-2 is greater than the amount of fibronectin in the matrix.

18 Claims, 4 Drawing Sheets

(56) References Cited

OTHER PUBLICATIONS

Abstract of "Development of a Neural Matrix for Enhanced Peripheral Nerve Repair," Wang, et al., Tissue Engineering Society International, 2003 Annual Meeting, Orlando, Florida.
Harley et al. Cells Tissues Organs.2004; 176(1-3): abstract. (Year: 2004).
Anonymous. Science Learning Hub [online]; 2007; downloaded from <URL https://www.sciencelearn.org.nz/resources/1006-insulation> on Nov. 19, 2018; 6 pages. (Year: 2007).
Sakamoto, "Further Development of Scaffolds for Regeneration of Nerves," Medical Design Briefs, May 2009.
Hattori "Alkali-Treated Collagen Retained the Triple Helical Conformation and the Ligand Activity for the Cell 7~dhesioin via a2b1 Integrin" Journal of Biochemistry. vol. 125. pp. 676-784. (1999); Abstract p. 676 Retrieved from https://www.jstage.jst.go.jp/article/biochemistry1922/125/4/125/4 676/ pdf/-char/en.

\* cited by examiner

DEVICES AND METHODS FOR NERVE REGENERATION

CROSS-REFERENCE TO RELATED APPLICATIONS

This application claims the benefit of the filing date of U.S. provisional application Ser. No. 63/005,585 filed Apr. 6, 2020, which is hereby incorporated by reference in its entirety.

FIELD OF THE INVENTION

The present invention relates to nerve regeneration devices and methods of making the same.

BACKGROUND OF THE INVENTION

Peripheral nerves (i.e. nerves within the peripheral nervous system, as opposed to the central nervous system) are susceptible to injury from trauma because of their widespread distribution through the body and vulnerable location throughout superficial and subcutaneous tissues. Such injury can potentially lead to complete loss of motor functionality and muscle paralysis, severely affecting an individual's quality of life. One treatment option for a severed nerve is by the direct suturing between the two stumps of the severed nerve. However, if the gap to be bridged between the two stumps of the severed nerve is beyond a certain size, such direct suturing is not viable. In these cases, autografts can be utilised, where tissue from one area of the body—the donor site—is delivered to a recipient site. However, use of autografts is hampered by limited availability of donor tissue. The prospects of success of autografts are also limited by the poor prognosis for recovery at both the donor tissue site and the recipient tissue site. As such nerve guidance conduits have been offered as an alternative to autografts. Such conduits are disclosed in U.S. Pat. No. 5,019,087 and are generally hollow and made of a bioresorbable material (i.e. a material that degrades in vivo). More recently, devices have become known where nerve guidance conduits are filled with a matrix material, and can be found together with their method of fabrication in US 2011/0129515, WO 2018/102812 and U.S. Pat. No. 4,955,893. Nerve guidance conduits such as these are inserted between two stumps of a severed nerve, and look to provide support and space for the nerve fibres to regrow between the stumps and so for the damaged nerves to regenerate. By facilitating nerve regeneration, such devices promote the repair of a severed nerve, without having to resort to autografts and their disadvantages. Although these devices have their merits, there are continuing challenges particularly for more serious injuries when the gap to be bridged in a severed nerve is particularly large. As such there remains room for improvement in nerve regeneration.

SUMMARY OF THE INVENTION

In a first aspect, there is a nerve regeneration device comprising a matrix contained within a bioresorbable conduit having a longitudinal axis, the matrix comprising elongate pores aligned with said longitudinal axis;
   the matrix comprising collagen, fibronectin, laminin-1, and laminin-2;
   wherein the amount, by weight, of laminin-1 or laminin-2 is greater than the amount of fibronectin in the matrix.

It has been surprisingly found that by careful tailoring of certain components of the matrix of the device, improved results are achieved which are indicative of improved nerve regeneration. As a result, the nerve regeneration device offers improved nerve repair over other available devices. It is thought that the increased amount of either laminin-1 or laminin-2 in relation to fibronectin in the collagen matrix encourages migrating neuronal cells to grow faster, thereby enhancing nerve regeneration. Additionally, this tailoring of components also encourages migrating neuronal cells to better express their own nerve growth inducing chemicals— this further enhances nerve repair without having to resort to artificially administered growth factors.

In a second aspect, there is a method of making the nerve regeneration device of the first aspect, comprising;
   providing a bioresorbable conduit with a longitudinal axis;
   filling the bioresorbable conduit with a slurry comprising collagen, fibronectin, laminin-1, and laminin-2, wherein the amount, by weight, of laminin-1 or laminin-2 is greater than the amount of fibronectin in the slurry;
   freezing the bioresorbable conduit and slurry such that there is a thermal gradient along the longitudinal axis, and substantially no thermal gradient perpendicular to said axis, thereby forming a frozen slurry having elongate crystals aligned with said axis, contained within the bioresorbable conduit;
   freeze drying the bioresorbable conduit and slurry to remove the crystals thereby forming a matrix comprising elongate pores aligned with said axis, contained within a bioresorbable conduit.

The method of the second aspect provides a convenient method of manufacture of the device disclosed herein.

BRIEF DESCRIPTION OF THE DRAWINGS

The performance of the present invention is shown in the following drawings.

DETAILED DESCRIPTION

Figure 1:
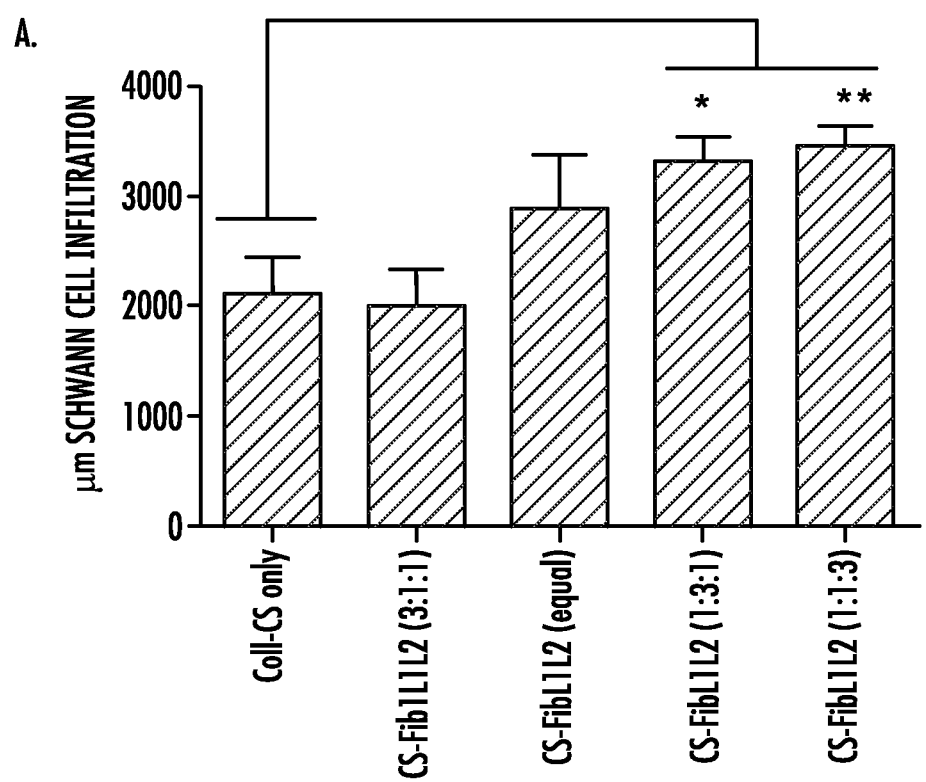
FIG. 1: Schwann cells growth

Disclosed herein, the nerve regeneration device comprises a matrix contained within a bioresorbable conduit. The term "bioresorbable" takes its usual definition of the art, and so refers to the ability to degrade in vivo. The bioresorbable conduit may be cross-linked, and the skilled person will appreciate that the rate of absorption in vivo of the conduit can be controlled by the degree of cross-linking imparted by chemical or physical treatment. The cross-linking can be done with chromium sulfate, formaldehyde, glutaraldehyde, carbodiimide, adipyl dichloride, and the like. Factors controlling the extent of crosslinking are the type and concentration of the cross-linking agent, the pH, and the temperature of incubation. The absorption rate of the collagen of the matrix can therefore be tailored accordingly. Preferably the bioresorbable conduit is comprised of collagen, which may possess intra- or intermolecular cross-linking. The bioresorbable conduit may even consist of collagen. As will be understood by the skilled person, collagen is a protein mostly found in fibrous tissue and constitutes the major protein of various connective tissues in the body. The collagen of the bioresorbable conduit may be Type I, Type II, Type III, Type IV, or Type V collagen, preferably Type I collagen. The collagen of the bioresorbable conduit may also be alkali-treated collagen. The bioresorbable conduit may comprise pores, which may for example have an average diameter of about 20 μm to about 200 μm, about 40 μm to about 180 μm, about 60 μm to about 160 μm, about 80 μm to about 140 μm, or about 100 μm to about 120 μm.

The bioresorbable conduit provides protection and structural support to the matrix. The term "conduit" takes its usual definition in the art and so refers to a hollow, open ended tube. The conduit has a longitudinal axis, which will be understood as referring to the axis that extends lengthways along the conduit, from end of the tube to the other. Once the nerve regeneration device is implanted in the body and positioned between two stumps of a severed nerve, the longitudinal axis of the conduit extends between the two stumps (and so corresponds with the axis of the severed nerve). The elongate pores of the matrix contained within the bioresorbable conduit are aligned with the conduit's longitudinal axis, and due to this alignment the elongate pores also extend between the two stumps of the severed nerve once the device is implanted in the body. The pores are elongate such that they provide a plurality of channels or pathways, generally spanning one end of the matrix to the other. The elongate nature of the pores together with their alignment facilitates the growth of nerve tissue into and through the matrix, as physical obstructions within the matrix are minimised as the nerve tissue propagates through.

It will be understood that the diameter of the elongate pores refers to their shortest dimension, and generally corresponds to the dimension substantially perpendicular to their longitudinal axis. The average diameter of the elongate pores can take a range of different values. For example, the elongate pores may have an average diameter of about 5 μm to about 360 μm, about 10 μm to about 300 μm, about 50 μm to about 250 μm, about 75 μm to about 200 μm, about 100 μm to about 200 μm, or about 160 μm to about 180 μm. In some instances the elongate pores may be tailored to the smaller end of these general ranges, e.g. the elongate pores may have an average diameter of about 50 μm to about 80 μm.

The matrix comprises collagen. It will be understood that collagen is a protein mostly found in fibrous tissue and constitutes the major protein of various connective tissues in the body. As the skilled person will understand, collagen is bioresorbable, and so can degrade in vivo. This allows the matrix to be absorbed in vivo as the tissue regenerates and grows into the matrix. The collagen may be cross-linked, and the skilled person will appreciate that the rate of absorption in vivo of the collagen can be controlled by the degree of intra- or intermolecular cross-linking imparted to the collagen by chemical or physical treatment. Factors controlling the extent of crosslinking are the type and concentration of the cross-linking agent, the pH, and the temperature of incubation. The absorption rate of the collagen of the matrix can therefore be tailored accordingly. The collagen in the matrix may be Type I, Type II, Type III, Type IV, or Type V collagen, preferably Type I collagen. The collagen of the matrix may also be alkali-treated collagen.

The matrix comprises fibronectin, laminin-1, and laminin-2. Fibronectin, laminin-1, and laminin-2 are macromolecules that can be found in vivo in the surrounding environment of the nerves. The presence of fibronectin, laminin-1, and laminin-2 in the matrix is thought to enhance neuronal growth and stimulate growth inducing protein expression. Disclosed herein, the amount, by weight, of laminin-1 or laminin-2 is greater than the amount of fibronectin in the matrix. This provides improved results, indicative of further improved nerve regeneration compared to when the laminin-1, laminin-2, and fibronectin are provided in the matrix in equal amounts. This is shown by the experimental data, where an increased amount of laminin-1 or an increased amount of laminin-2 vs the amount of fibronectin displays increased propagation of Schwann cells, increased expression of nerve growth factor (NGF), and increased βIII Tub expression. These results are indicative of an improved ability to promote the growth of nerve fibres. The experimental data also demonstrates that the ratios of components disclosed herein provide generally adequate and acceptable secretion of vascular endothelial growth factor (VEGF), which indicates that such ratios of components facilitate a suitable blood supply to the regenerating nerve.

Figure 3:
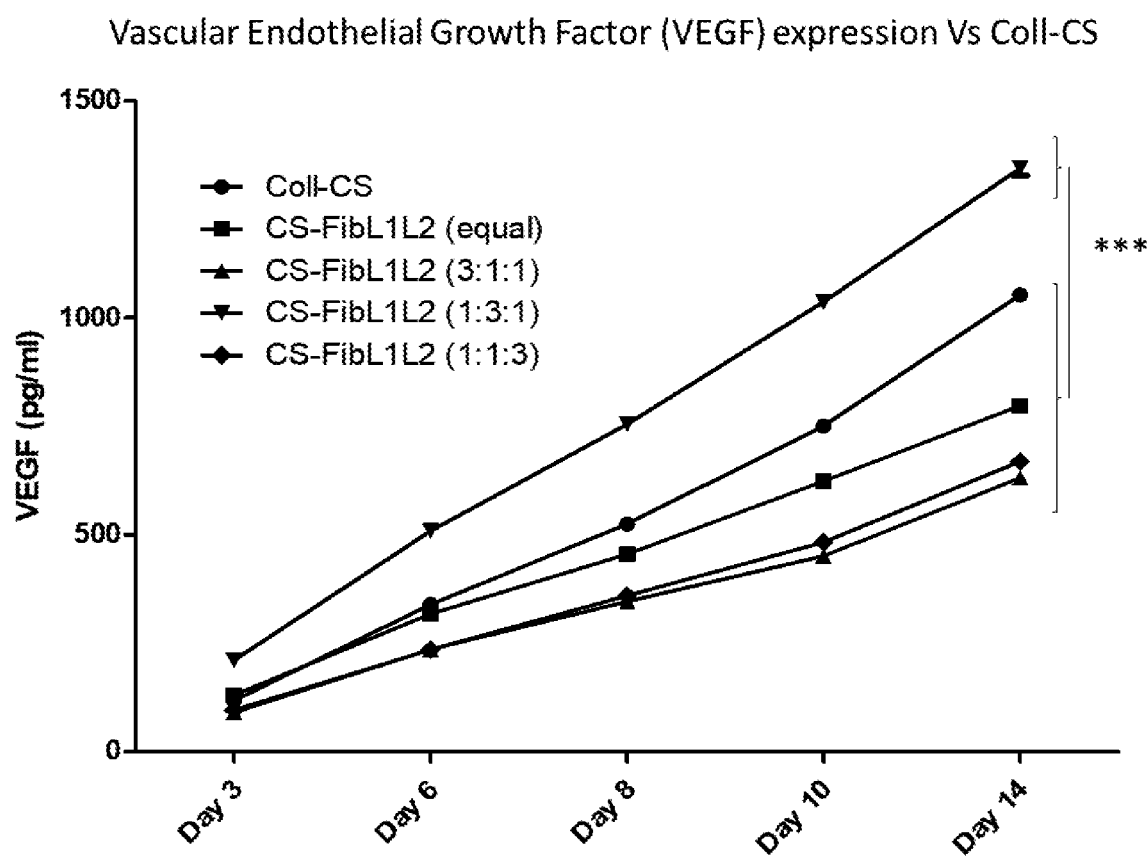
FIG. 3: expression of vascular endothelial growth factor (VEGF)

Building on the existing improvement provided by the ratios of component disclosed herein, the experimental data also shows that an increased amount of laminin 1 vs both laminin 2 and fibronectin represents a particularly optimal scenario. FIG. 3 shows that an increased amount of laminin 1 vs both laminin 2 and fibronectin provides an additional improvement in the secretion of vascular endothelial growth factor (VEGF), indicative of an additional improvement in blood supply to the regenerating nerve.

Preferably, the amount, by weight, of laminin-1 or laminin-2 is at least twice as great as the amount of fibronectin in the matrix. In other words, preferably the ratio, by weight, of laminin-1:fibronectin is at least 2:1, or the ratio of laminin-2:fibronectin is at least 2:1, in the matrix. More preferably, the amount, by weight, of laminin-1 or laminin-2 is at least three times as great as the amount of fibronectin in the matrix. In other words, preferably the ratio, by weight, of laminin-1:fibronectin is at least 3:1, or the ratio of laminin-2:fibronectin is at least 3:1, in the matrix. The maximum amounts of laminin-1 or laminin-2 relative to fibronectin can generally be varied as appropriate. Preferably, the amount, by weight, of laminin-1 or laminin-2 is at most 10 times, more preferably at most 8 times, more preferably at most 6 times as great as the amount of fibronectin in the matrix. In other words: preferably the ratio, by weight, of laminin-1:fibronectin is at most 10:1, or the ratio, by weight, of laminin-2:fibronectin is at most 10:1, in the matrix; more preferably the ratio, by weight, of laminin-1:fibronectin is at most 8:1, or the ratio, by weight, of laminin-2:fibronectin is at most 8:1, in the matrix; more preferably the ratio, by weight, of laminin-1:fibronectin is at most 6:1, or the ratio, by weight, of laminin-2:fibronectin is at most 6:1, in the matrix.

Preferably, the amount, by weight, of laminin-1 is greater than the amount of fibronectin in the matrix, and the amount, by weight, of laminin-1 is also greater than the amount of laminin-2 in the matrix. This relative weighting of increased laminin-1 in particular provides the additional improvement of enhanced blood supply to the regenerating nerve. Here, it is preferable that the amount, by weight, of laminin-1 is at least twice as great as the amount of fibronectin in the matrix, and the amount, by weight, of laminin-1 is also at least twice as great as the amount of laminin-2 in the matrix. More preferably, the amount, by weight, of laminin-1 is at least three times as great as the amount of fibronectin in the matrix, and the amount, by weight, of laminin-1 is also at least three times as great as the amount of laminin-2 in the matrix. In other words, the amount of laminin-1 in the ratio of fibronectin:laminin-1:laminin-2 in the matrix is preferably at least 1:2:1, more preferably at least 1:3:1. The maximum amount of laminin-1 relative to both laminin-2 and fibronectin in the matrix can generally be varied as appropriate, but preferably the amount, by weight, of laminin-1 is at most 10 times, more preferably at most 8 times, more preferably at most 6 times, as great as the amount of fibronectin in the matrix, and at most 10 times, more preferably at most 8 times, more preferably at most 6 times, as great as the amount of laminin-2 in the matrix. In other words, the amount, by weight, of laminin-1 in the ratio of fibronectin:laminin-1:laminin-2 in the matrix is preferably at most 1:10:1, more preferably at most 1:8:1, more preferably at most 1:6:1.

In an exemplary embodiment, the amount, by weight, of laminin-2 in the ratio of fibronectin:laminin-1:laminin-2 in the matrix is at least 1:1:3, preferably in the range of 1:1:3 to 1:1:4.

Optimally, the amount, by weight, of laminin-1 in the ratio of fibronectin:laminin-1:laminin-2 in the matrix is at least 1:3:1, preferably in the range of 1:3:1 to 1:4:1, said ratio range providing the additional improvement of enhanced blood supply to the regenerating nerve, as shown in the experimental data.

The matrix preferably further comprises a glycosaminoglycan, such as chondroitin sulfate, dermatan sulfate, keratin sulfate, hyaluronic acid, or combinations thereof. Preferably, the matrix comprises chondroitin sulfate, such as chondroitin-6-sulfate. The collagen and the glycosaminoglycan may be cross-linked. Cross-linking can be achieved by heating under vacuum or by treatment with chemical cross-linking agents, e.g., glutaraldehyde, formaldehyde, chromium sulfate, carbodiimide, adipyl dichloride, and the like.

The nerve regeneration device is generally cylindrical. The exact dimensions of the nerve regeneration device can be tailored depending on the particular nature of the nerve damage to be repaired. For example the length of the nerve regeneration device can be tailored depending on the length of the nerve gap to be bridged, and the diameter of the nerve regeneration device can be tailored depending on the diameter of the damaged nerve. The resorption rate of the nerve regeneration device can also be varied as desired. For example, the nerve regeneration device may be tailored (by cross-linking of the materials in question) to such an extent that they are completely resorbed within about 1 to about 3 months.

The matrix and the bioresorbable conduit may have the same length, such that the matrix is flush with each end of the conduit. Or, the matrix may have a different length to that of the bioresorbable conduit; here, the matrix may be recessed within one or both ends of the conduit, or the matrix may extend beyond one or both ends of the conduit, if desired. The total length of the nerve regeneration device refers to the full length extending from one terminus of the nerve regeneration device to the other. The total length of the nerve regeneration device can vary from about 1 cm to about 20 cm, from about 1 cm to about 15 cm, from about 2 cm to about 10 cm, or from about 2 cm to about 6 cm.

The length of the bioresorbable conduit can be tailored depending on the length of the nerve gap to be bridged, and can vary from about 1 cm to about 20 cm, from about 1 cm to about 15 cm, from about 2 cm to about 10 cm, or from about 2 cm to about 6 cm. The inner diameter of the bioresorbable conduit can be tailored depending on the diameter of the damaged nerve, and can vary from about 1 mm to about 15 mm, from about 1.5 mm to about 10 mm, or about 1.5 mm to about 5.0 mm. The wall thickness of the bioresorbable conduit can vary and can be tailored to balance a desired permeability with enough compressive strength to prevent collapse. Preferably, the bioresorbable conduit has walls as thin as possible while still withstanding suturing and collapse when used in vivo. For example, the bioresorbable conduit has a wall thickness in the range of from about 0.2 mm to about 1.2 mm, e.g. about 0.1 mm to about 0.8 mm. The bioresorbable conduit is preferably less porous than the matrix.

The diameter of the matrix is such that it generally extends across the entire internal diameter of the bioresorbable conduit. The diameter can be tailored depending on the diameter of the damaged nerve, and can vary from about 1 mm to about 15 mm, from about 1.5 mm to about 10 mm, or about 1.5 mm to about 5.0 mm. The length of the matrix can be tailored depending on the length of the nerve gap to be bridged, and can vary from about 1 cm to about 20 cm, from about 1 cm to about 15 cm, from about 2 cm to about 10 cm, or from about 2 cm to about 6 cm.

Connectors may be used to connect the conduit containing the matrix, or the matrix alone, to the severed end of a nerve. Suitable connectors within the scope of the present invention overlap the conduit and the nerve and include wraps or cuffs with or without sutures or any other suitable connector design that can be used to connect the conduit or matrix to the severed end of a nerve.

One particular example of a connector is a collagen sheet or wrap that can be placed or wrapped around the nerve and the device and then secured in place, such as by using sutures. One such collagen sheet or wrap is marketed under the NEURAWRAP mark from Integra LifeSciences Corporation, Plainsboro, N.J. Such sheets or wraps can be in a cylindrical form having a longitudinal slit where opposing ends of the wrap can be pulled apart, the nerve inserted and then the wrap can rebound into a cylindrical position around the nerve. Such sheets or wraps can be made from bioresorbable materials such as collagen, laminin-1, fibronectin, laminin-2, hyaluronic acid, chitin, chitosan, keratin, polyglycolic acid, polylactic acid, cellulose and the like. The materials can be used alone or in combination with each other.

Where the matrix is flush with an end of the conduit, another suitable connector is a cuff having a first open end and a second open end. The cuff has an outer diameter larger than the outer diameter of the conduit. The cuff conforms to the outer shape of the conduit. For example, if the conduit is cylindrical, the cuff will be a cylindrical cuff. A cuff is placed onto the outer end of the conduit with a portion of the cuff extending over the end of the conduit. The first end of the severed nerve is inserted into the cuff extension and is brought into contact with the first end of the matrix to form a first junction between the severed nerve and the conduit. The nerve, cuff and conduit are all secured in place at this first junction according to methods known to those skilled in the art, such as suturing. The second end of the severed nerve is brought into contact with the second end of the matrix to form a second junction between the severed nerve and the conduit. This junction may also be secured in place with a cuff as described above. Cuffs according to embodiments of the present invention can be formed from various materials including collagen laminin-1, fibronectin, laminin-2, hyaluronic acid, chitin, chitosan, keratin, polyglycolic acid, polylactic acid, cellulose and the like. The materials can be used alone or in combination with each other. Suitable commercially available cuffs include bioresorbable collagen tubes having a length sufficient for a cuff, as are commercially available under the brand name NEURAGEN from Integra LifeSciences Corporation, Plainsboro, N.J. Methods for making certain exemplary embodiments of the resorbable tube are disclosed in U.S. Pat. No. 5,019,087, which is incorporated herein by reference in its entirety.

If, according to an exemplary embodiment, the matrix is recessed within one or both ends of the conduit, i.e. the end of the conduit extends past the matrix therein, the severed nerve is introduced into the conduit until it contacts the matrix to form a junction and the nerve is secured in place within the conduit using methods known to those skilled in the art, such as suturing. No connector such as a sheet, wrap or cuff is required with this exemplary embodiment, although a sheet, wrap or cuff could still be used if desired.

Also disclosed herein is a method of making the nerve regeneration device disclosed herein. This comprises the steps of:
- providing a bioresorbable conduit with a longitudinal axis;
- filling the bioresorbable conduit with a slurry comprising collagen, fibronectin, laminin-1, and laminin-2, wherein the amount, by weight, of laminin-1 or laminin-2 is greater than the amount of fibronectin in the slurry;
- freezing the bioresorbable conduit and slurry such that there is a thermal gradient along the longitudinal axis, and substantially no thermal gradient perpendicular to said axis, thereby forming a frozen slurry having elongate crystals aligned with said axis, contained within the bioresorbable conduit;
- freeze drying the bioresorbable conduit and slurry to remove the crystals thereby forming a matrix comprising elongate pores aligned with said axis, contained within a bioresorbable conduit.

It will be understood that any possible, preferred, exemplary or optimal features disclosed herein in the context of the nerve regeneration device can be applied to the method of making said device.

The bioresorbable conduit provided as part of the method corresponds with the bioresorbable conduit of the nerve regeneration device disclosed herein. Accordingly, any possible, preferred, exemplary or optimal features disclosed elsewhere in relation to the bioresorbable conduit can be applied in the context of the method disclosed herein.

During the method, a slurry comprising collagen, fibronectin, laminin-1, and laminin-2 is formed, and this slurry goes on to form the matrix disclosed herein. Accordingly any possible, preferred, exemplary or optimal features disclosed elsewhere in relation to the matrix can be applied in the context of the method disclosed herein.

During the method the bioresorbable conduit and slurry are subjected to a freezing step such that there is a thermal gradient along the longitudinal axis, and substantially no thermal gradient perpendicular to said axis. This may be achieved by positioning a thermally conducting plug at one end of the conduit, thereby creating a thermal gradient along its longitudinal axis, and then encasing the conduit and the slurry in a thermally insulating housing so as to minimise or eliminate completely any thermal gradient perpendicular to said axis. The plug acts as a heat sink whereby heat is drawn out of the slurry along the longitudinal axis by the heat sink. The plug can be made of any material that has high thermal conductivity, such as metals and metal alloys (e.g., brass, steel, copper, zinc, nickel, and aluminum, among others). It is thought that this step results in the formation of elongate crystals in a frozen slurry aligned with the longitudinal axis. After a freeze drying step, these crystals are removed to leave elongate pores as disclosed herein.

During the freezing step heat transfer occurs from the slurry to a cooling medium, which can include any solid or liquid media capable of freezing the liquid slurry, for example, a cooling medium that maintains a temperature between about −40° C. and about −196° C. The cooling medium may be at least one of liquid nitrogen, dry ice, an isopropanol/dry ice mixture, and silicone oil cooled by liquid nitrogen. The cooling media can be used alone or in combination with each other.

The following non-limiting examples illustrate the invention.

EXAMPLES

An initial slurry of micro-fibrillar collagen and chondroitin-6-sulphate was blended at a chondroitin-6-sulphate concentration 50 µg/ml. In a separate 50 ml tube, solutions of fibronectin, laminin 1 and laminin 2 were pipetted at a series of ratios to a total fibronectin+laminin 1+laminin 2 concentration of 5 µg/ml. The ratios used were as follows:
- 3.3 µg Fibronectin: 0.85 µg laminin 1:0.85 µg laminin 2 (3.88:1:1, referred to on the figures as "3:1:1" purely for shorthand purposes)
- 0.85 µg Fibronectin: 3.3 µg laminin 1:0.85 µg laminin 2 (1:3.88:1, referred to on the figures as "1:3:1" purely for shorthand purposes)
- 0.85 µg Fibronectin: 0.85 µg laminin 1:3.3 µg laminin 2 (1:1:3.88, referred to on the figures as "1:1:3" purely for shorthand purposes)
- 1.67 µg Fibronectin: 1.67 µg laminin 1:1.67 µg laminin 2 (equal ratio i.e. 1:1:1)

The fibronectin, laminin 1 and laminin 2 were mixed thoroughly into the collagen-chondroitin-6-sulphate slurry and transferred to a 10 ml syringe where the mixture was degassed thoroughly under vacuum.

The slurry was then loaded into a non-conductive cylindrical mould and subjected to axial freezing. A cooling gradient was generated perpendicular to the freeze dryer shelf using unidirectional heat-transfer via a thermally conducting plug at the base of cylindrical mould containing the slurry. The thermally conducting plug allows a unidirectional cooling gradient which has minimal radial components. Heat transfer was achieved by a rapid cooling of the slurry by immersion in liquid nitrogen for 30 seconds before placing the moulds on a freeze dryer shelf that has been cooled to −40° C. and initiating the freeze drying cycle. Cooling in this manner formed substantially parallel, axially aligned ice crystals in the slurry. Following a freeze drying step, a matrix was formed with axially aligned elongate pores.

Figure 2:
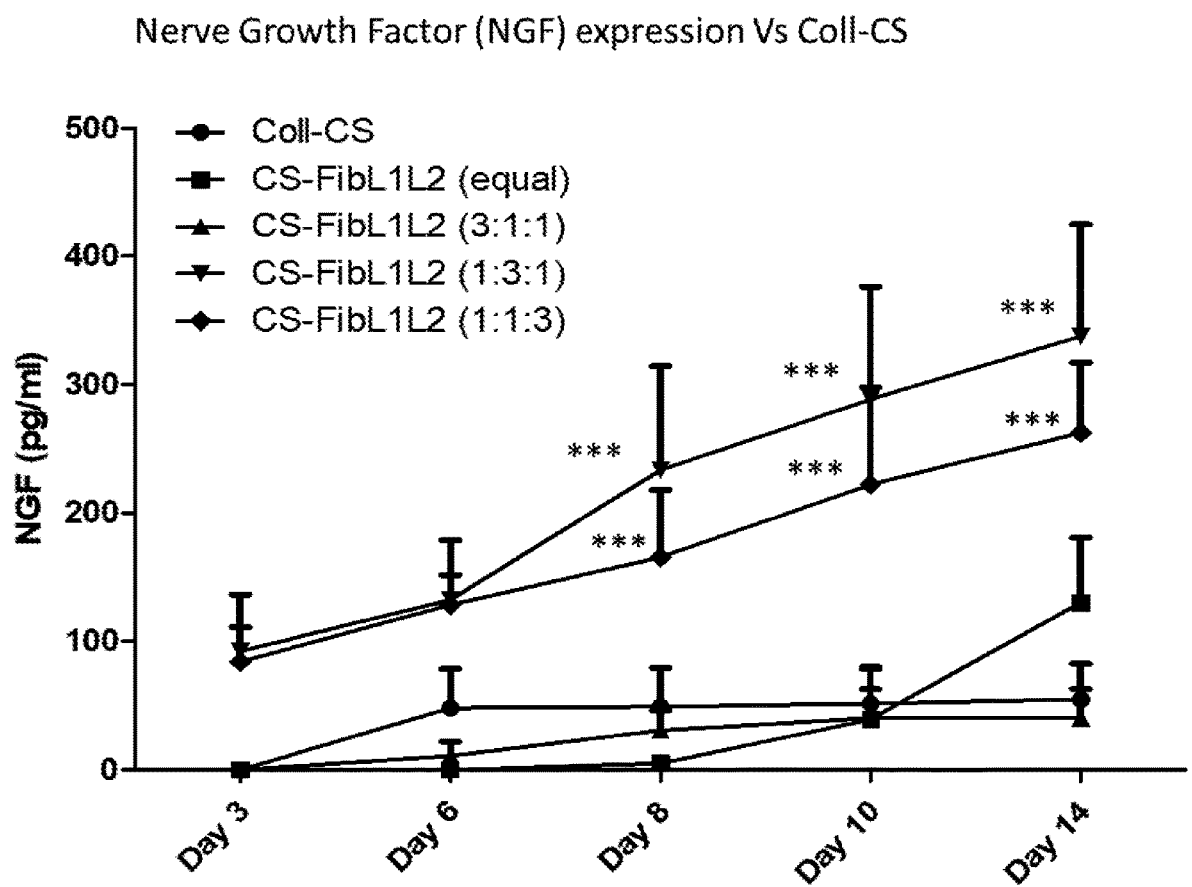
FIG. 2: expression of nerve growth factor (NGF)
Figure 4:
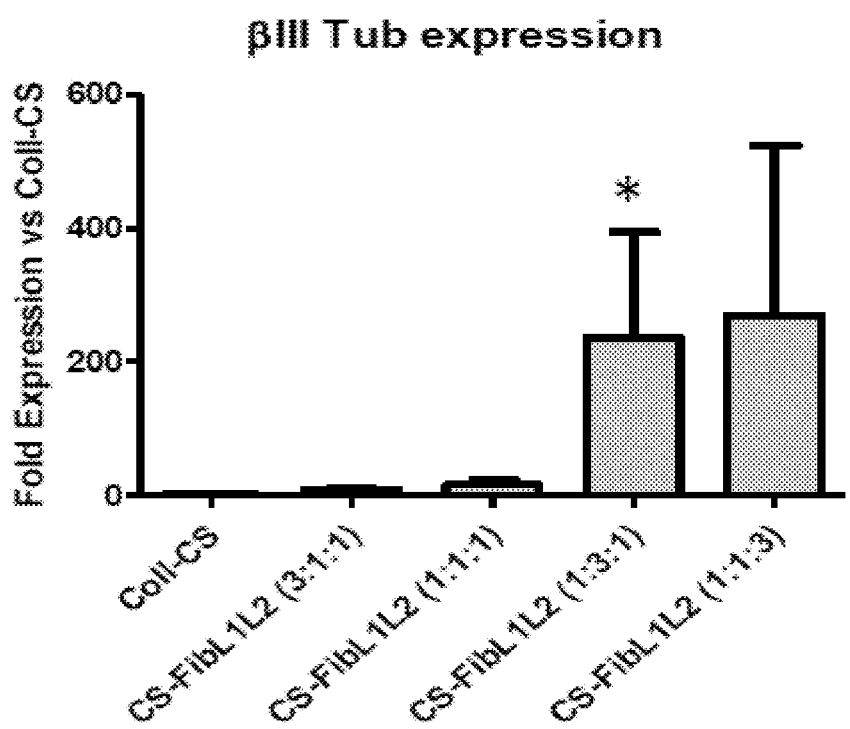
FIG. 4: βIII Tub expression.

The performance of the matrix was then assessed by examining rat dorsal root ganglia grown on the matrix. The results are shown in FIGS. 1-4 as follows:
- FIG. 1: Schwann cells growth
- FIG. 2: expression of nerve growth factor (NGF)
- FIG. 3: expression of vascular endothelial growth factor (VEGF)
- FIG. 4: βIII Tub expression FIGS. 1, 2, and 4 show a notable improvement in the growth of Schwann cells, the expression of nerve growth factor, and µIII Tub expression, when the amount of laminin 1 or laminin 2 is increased vs the amount of fibronectin, with improved results being achieved compared to the scenario where the laminin 1, laminin 2, and fibronectin are present in equal amounts. These results are indicative of an improved ability to promote the growth of nerve fibres. In addition to this, FIG. 3 shows that all ratios of components disclosed herein provide generally adequate and acceptable secretion of vascular endothelial growth factor (VEGF), which indicates that such ratios of components facilitate a suitable blood supply to the regenerating nerve.

Building on the existing improvement provided by the ratios of component disclosed herein, FIG. 3 shows that an increased amount of laminin 1 vs both laminin 2 and fibronectin represents a particularly optimal scenario. FIG. 3 shows that an increased amount of laminin 1 vs both laminin 2 and fibronectin provides an additional improvement in the secretion of vascular endothelial growth factor (VEGF), indicative of an additional improvement in blood supply to the regenerating nerve.

On balance the results in this body of data indicate that an increased amount of laminin 1 or laminin 2 vs fibronectin provides improved nerve regeneration, with an increased amount of laminin 1 vs both laminin 2 and fibronectin representing a particularly optimal scenario.

The invention claimed is:

1. A nerve regeneration device comprising a matrix contained within a bioresorbable conduit having a longitudinal axis, the matrix comprising elongate pores aligned with said longitudinal axis;
the matrix comprising collagen, fibronectin, laminin-1, and laminin-2;
wherein the amount by weight of fibronectin:laminin-1:laminin-2 in the matrix is 1:3:1.

2. The nerve regeneration device of claim 1, wherein the amount, by weight, of laminin-1 or laminin-2 is at least twice as great as the amount of fibronectin in the matrix.

3. The nerve regeneration device of claim 1, wherein the amount, by weight, of laminin-1 or laminin-2 is at least three times as great as the amount of fibronectin in the matrix.

4. The nerve regeneration device of claim 1, wherein the amount, by weight, of laminin-1 is greater than the amount of fibronectin in the matrix; and the amount, by weight, of laminin-1 is greater than the amount of laminin-2 in the matrix.

5. The nerve regeneration device of claim 1, wherein the matrix further comprises a glycosaminoglycan.

6. The nerve regeneration device of claim 5, wherein the glycosaminoglycan is chondroitin sulfate, dermatan sulfate, keratin sulfate, hyaluronic acid, or combinations thereof.

7. The nerve regeneration device of claim 6, wherein the glycosaminoglycan is chondroitin sulfate.

8. The nerve regeneration device of claim 1, wherein the pores of the matrix have an average diameter of about 10 μm to about 300 μm.

9. The nerve regeneration device of claim 1, wherein the pores of the matrix have an average diameter of about 50 μm to about 80 μm.

10. The nerve regeneration device of claim 1, wherein the bioresorbable conduit is comprised of collagen.

11. The nerve regeneration device of claim 1, wherein the bioresorbable conduit comprises pores with an average diameter of about 100 μm to about 200 μm.

12. The nerve regeneration device of claim 1, wherein the bioresorbable conduit has an internal diameter from about 1.5 mm to about 5.0 mm.

13. The nerve regeneration device of claim 1, wherein said device has a length from about 1 cm to about 20 cm.

14. A method of making the nerve regeneration device of claim 1, comprising;
providing a bioresorbable conduit with a longitudinal axis;
filling the bioresorbable conduit with a slurry comprising collagen, fibronectin, laminin-1, and laminin-2, wherein the amount by weight of fibronectin:laminin-1:laminin-2 in the matrix is 1:3:1;
freezing the bioresorbable conduit and slurry such that there is a thermal gradient along the longitudinal axis, and substantially no thermal gradient perpendicular to said axis, thereby forming a frozen slurry having elongate crystals aligned with said axis, contained within the bioresorbable conduit;
freeze drying the bioresorbable conduit and slurry to remove the crystals thereby forming a matrix comprising elongate pores aligned with said axis, contained within a bioresorbable conduit.

15. The method of claim 14, wherein the amount, by weight, of one or the other of laminin-1 or laminin-2 is at least twice as great as the amount of fibronectin in the slurry.

16. The method of claim 14, wherein the amount, by weight, of laminin-1 or laminin-2 is at least three times as great as the amount of fibronectin in the matrix.

17. The method of claim 14, wherein the amount, by weight, of laminin-1 is greater than the amount of fibronectin in the slurry; and the amount, by weight, of laminin-1 is greater than the amount of laminin-2 in the slurry.

18. The method of claim 14, wherein the pores of the matrix have an average diameter of about 10 μm to about 300 μm.

* * * * *